United States Patent
Lange et al.

(10) Patent No.: US 6,974,810 B2
(45) Date of Patent: Dec. 13, 2005

(54) 4,5-DIHYDRO-1H-PYRAZOLE DERIVATIVES HAVING POTENT $CB_1$-ANTAGONISTIC ACTIVITY

(75) Inventors: Josephus H. M. Lange, Weesp (NL); Cornelis G. Kruse, Weesp (NL); Jacobus Tipker, Weesp (NL); Herman H. van Stuivenberg, Weesp (NL); Arnoldus H. J. Herremans, Weesp (NL)

(73) Assignee: Solvay Pharmaceuticals B.V., Weesp (NL)

( * ) Notice: Subject to any disclaimer, the term of this patent is extended or adjusted under 35 U.S.C. 154(b) by 0 days.

(21) Appl. No.: 10/472,529

(22) PCT Filed: Sep. 17, 2002

(86) PCT No.: PCT/EP02/10435

§ 371 (c)(1),
(2), (4) Date: Sep. 24, 2003

(87) PCT Pub. No.: WO03/026648

PCT Pub. Date: Apr. 3, 2003

(65) Prior Publication Data

US 2004/0106800 A1 Jun. 3, 2004

(30) Foreign Application Priority Data

Sep. 21, 2001 (EP) ............................................. 01203849

(51) Int. Cl.[7] .................. A61K 31/415; A61K 31/4155; C07D 231/06; C07D 401/12; C07D 413/06
(52) U.S. Cl. .................... 514/236.5; 514/326; 514/403; 544/140; 546/211; 548/379.4
(58) Field of Search ....................... 548/379.4; 546/211; 544/140; 514/236.5, 326, 403

(56) References Cited

U.S. PATENT DOCUMENTS

| 4,070,365 A | 1/1978 | van Daalen et al. |
| 5,624,941 A | 4/1997 | Barth et al. |

FOREIGN PATENT DOCUMENTS

| WO | WO 00/46209 | 8/2000 |
| WO | WO 01/70700 A1 | 9/2001 |

OTHER PUBLICATIONS

Pertwee; "Pharmacology of Cannabinoid Receptor Ligands"; Current Medicinal Chemistry, vol. 6, No. 8, pp. 635–664, (1999).

Jochen Antel et al., "Novel Medical Uses of Compounds Showing CB1–Antagonistic Activity and Combination Treatment Involving Said Compounds," US–10/969,840, filed on Oct. 22, 2004.

Jochen Antel et al., "Novel Medical Combination Treatment of Obesity Involving 4,5–Dihydro–1H–Pyrazole Derivatives Having CB1–Antagonistic Activity," US–10/972,006, filed on Oct. 25, 2004.

Jochen Antel et al., "Novel Medical Combination Treatment of Obesity Involving 4,5–Dihydro–1H–Pyrazole Derivatives Having CB1–Antagonistic Activity," US–11/005,486, filed on Dec. 7, 2004.

*Primary Examiner*—Laura L. Stockton
(74) *Attorney, Agent, or Firm*—Finnegan, Henderson, Farabow, Garrett & Dunner, L.L.P.

(57) ABSTRACT

The present invention relates to a group of novel 4,5-dihydro-1H-pyrazole derivatives which are potent cannabinoid ($CB_1$) receptor antagonists with utility for the treatment of diseases connected with disorders of the cannabinoid system. The compounds have the general formula (Ia) or (Ib) wherein the symbols have the meanings given in the specification. The invention also relates to methods for the preparation of these compounds, and to pharmaceutical compositions containing one or more of these compounds as an active component

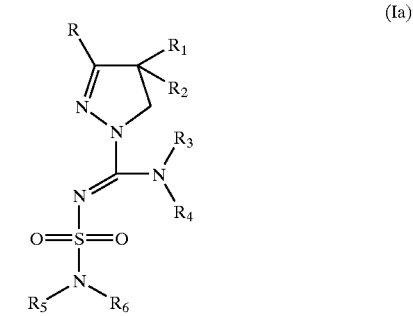

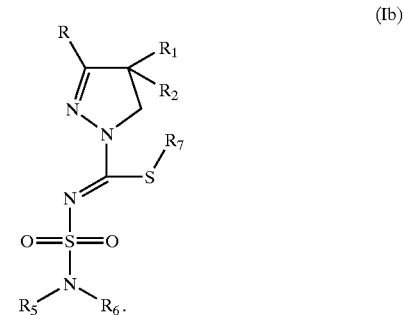

9 Claims, No Drawings

4,5-DIHYDRO-1H-PYRAZOLE DERIVATIVES HAVING POTENT CB₁-ANTAGONISTIC ACTIVITY

The present invention relates to a group of novel 4,5-dihydro-1H-pyrazole derivatives, to methods for the preparation of these compounds, and to pharmaceutical compositions containing one or more of these compounds as an active component.

The above mentioned 4,5-dihydro-1H-pyrazoles are potent cannabinoid ($CB_1$) receptor antagonists with utility for the treatment of disorders involving cannabinoid neurotransmission.

Cannabinoids are present in the Indian hemp *Cannabis saliva* and have been used as medicinal agents for centuries (Mechoulam, R. and Feigenbaum, J. J. *Prog. Med. Chem.* 1987, 24, 159). However, only within the past ten years the research in the cannabinoid area has revealed pivotal information on cannabinoid receptors and their (endogenous) agonists and antagonists. The discovery and the subsequent cloning of two different subtypes of cannabinoid receptors ($CB_1$ and $CB_2$) stimulated the search for novel cannabinoid receptor antagonists (Munro, S. et al., *Nature* 1993, 365, 61. Matsuda, L. A. and Bonner, T. I. *Cannabinoid Receptors*, Pertwee, R. G. Ed. 1995, 117, Academic Press, London). In addition, pharmaceutical companies became interested in the development of cannabinoid drugs for the treatment of diseases connected with disorders of the cannabinoid system (Consroe, P. *Neurobiology of Disease* 1998, 5, 534. Pop, E. *Curr. Opin. In CPNS Investigational Drugs* 1999, 1, 587. Greenberg, D. A. *Drug News Perspect.* 1999, 12, 458. Pertwee, R. G., *Progress in Neurobiology* 2001, 63, 569). Hitherto, several $CB_1$ receptor antagonists are known. Sanofi disclosed their diarylpyrazole congeners as selective $CB_1$ receptor antagonists. A representative example is SR-141716A (Dutta, A. K. et al, *Med. Chem. Res.* 1994, 5, 54. Lan, R. et al., *J. Med. Chem.* 1999, 42, 769. Nakamura-Palacios, E. M. et al., *CNS Drug Rev.* 1999, 5, 43). CP-272871 is a pyrazole derivative, like SR141716A, but less potent and less $CB_1$ receptor subtype-selective than SR141716A (Meschler, J. P. et al., *Biochem. Pharmacol.* 2000, 60, 1315). Aminoalkylindoles have been disclosed as $CB_1$ receptor antagonists. A representative example is Iodopravadoline (AM-630), which was introduced in 1995. AM-630 is a moderately active $CB_1$ receptor antagonist, but sometimes behaves as a weak partial agonist (Hosohata, K. et al., *Life Sc.* 1997, 61, PL115). Researchers from Eli Lilly described aryl-aroyl substituted benzofurans as selective $CB_1$ receptor antagonists (e.g. LY-320135) (Felder, C. C. et al., *J. Pharmacol. Exp. Ther.* 1998, 284, 291). 3-Alkyl-5, 5'-diphenylimidazolidinediones were described as cannabinoid receptor ligands, which were indicated to be cannabinoid antagonists (Kanyonyo, M. et al., *Biorg. Med. Chem. Lett.* 1999, 9, 2233). Aventis Pharma claimed diarylmethyleneazetidine analogs as $CB_1$ receptor antagonists (Mignani, S. et al., Patent FR 2783246, 2000; *Chem. Abstr.* 2000, 132, 236982). Tricyclic pyrazoles were claimed by Sanofi-Synthelabo as $CB_1$ antagonists (Barth, F. et al., Patent WO 0132663, 2001; *Chem. Abstr.* 2001, 134, 340504). Interestingly, many $CB_1$ receptor antagonists have been reported to behave as inverse agonists in vitro (Landsman, R. S. et al., *Eur. J. Pharmacol.* 1997, 334, R1). Reviews provide a nice overview of the cannabinoid research area (Mechoulam, R. et al., *Prog. Med. Chem.* 1998, 35, 199. Lambert, D. M. *Curr. Med. Chem.* 1999, 6, 635. Mechoulam, R. et al., *Eur. J. Pharmacol.* 1998, 359, 1. Williamson, E. M. and Evans, F. J. *Drugs* 2000, 60, 1303. Pertwee, R. G. *Addiction Biology* 2000, 5, 37. Robson, P. *Br. J. Psychiatry* 2001, 178, 107. Pertwee, R. G. *Prog. Neurobiol.* 2001, 63, 569. Goya, P and Jagerovic, N. *Exp. Opin. Ther. Patents* 2000, 10, 1529. Pertwee, R. G. *Gut* 2001, 48, 859).

It has now surprisingly been found that potent and selective antagonism of cannabinoid-$CB_1$ receptors is present in the novel 4,5-dihydro-1H-pyrazole derivatives of the formula (Ia) or (Ib), prodrugs thereof, tautomers thereof and salts thereof

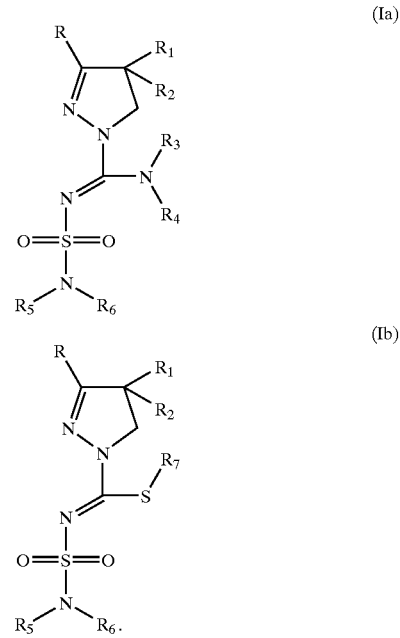

wherein

R and $R_1$ independently represent phenyl, thienyl or pyridyl which groups may be substituted with 1, 2 or 3 substituents Y, which can be the same or different, from the group $C_{1-3}$-alkyl or alkoxy, hydroxy, halogen, trifluoromethyl, trifluoromethylthio, trifluoromethoxy, nitro, amino, mono- or dialkyl ($C_{1-2}$)-amino, mono- or dialkyl ($C_{1-2}$)-amido, ($C_{1-3}$)-alkyl sulfonyl, dimethylsulfamido, $C_{1-3}$-alkoxycarbonyl, carboxyl, trifluoromethylsulfonyl, cyano, carbamoyl, sulfamoyl and acetyl, or R and/or $R_1$ represent naphtyl, $R_2$ represents hydrogen, hydroxy, $C_{1-3}$-alkoxy, acetyloxy or propionyloxy, $R_3$ represents a hydrogen atom or a branched or unbranched $C_{1-8}$ alkyl group or a $C_{3-7}$ cycloalkyl group which alkyl group or cycloalkyl group may be substituted with a hydroxy group, $R_4$ represents a hydrogen atom or a branched or unbranched $C_{1-8}$ alkyl, $C_{3-8}$ cycloalkyl, $C_{2-10}$ heteroalkyl, $C_{3-8}$ nonaromatic heterocycloalkyl or $C_{4-10}$ nonaromatic heterocycloalkyl-alkyl moiety which moieties may contain one or more heteroatoms from the group (O, N, S), which moieties may be substituted with a keto group, trifluoromethyl group, $C_{1-3}$ alkyl group, hydroxy, amino, monoalkylamino, or dialkylamino group or a fluoro atom, or $R_4$ represents an amino, hydroxy, phenoxy or benzyloxy group or $R_4$ represents a branched or unbranch d $C_{1-8}$ alkoxy, $C_{3-8}$ alkenyl, $C_{5-8}$ cycloalk nyl or $C_{6-9}$ cycloalkenylalkyl group which groups may contain a sulphur, nitrogen or oxygen atom, a keto group or —SO$_2$— group which C$_{1-8}$ alkoxy, C$_{3-8}$ alkenyl, C$_{5-8}$ cycloalkenyl or C$_{6-9}$ cycloalkenylalkyl groups may be substituted with a hydroxy group, a trifluoromethyl group, an amino group, a monoalkylamino group or dialkylamino group or a fluoro atom, or R$_4$ represents a phenyl, benzyl, pyridyl, thienyl, pyridylmethyl or phenethyl group wherein the aromatic rings may be substituted with 1, 2 or 3 of the substituents Y, wherein Y has the meaning as indicated above, or R$_4$ represents a group NR$_8$R$_9$ with the proviso that R$_3$ represents a hydrogen atom or a methyl group and wherein R$_8$ and R$_9$ are the same or different and represent C$_{1-4}$ alkyl or C$_{2-4}$ trifluoroalkyl or R$_8$ and R$_9$—together with the nitrogen atom to which they are bonded—form a saturated or un-saturated heterocyclic moiety having 4 to 8 ring atoms which heterocyclic moiety may contain an oxygen or sulphur atom or a keto group or —SO$_2$— group or an additional nitrogen atom, which saturated or unsaturated heterocyclic moiety may be substituted with a C$_{1-4}$ alkyl group or R$_3$ and R$_4$—together with the nitrogen atom to which they are bonded—form a saturated or unsaturated, monocyclic or bicyclic heterocyclic moiety having 4 to 10 ring atoms, which heterocyclic moiety may contain one or more atoms from the group (O, N, S) or a keto group or —SO$_2$— group, which moiety may be substituted with a C$_{1-4}$ alkyl, hydroxyalkyl, phenyl, thienyl, pyridyl, amino, monoalkylaminoalkyl, dialkylaminoalkyl, monoalkylamino, dialkylamino, aminoalkyl, azetidinyl, pyrrolidinyl, piperidinyl or hexahydro-1H-azepinyl group, R$_5$ and R$_6$ independently of each other represent a hydrogen atom or a branched or unbranched C$_{1-8}$ alkyl or alkenyl group which groups may contain one or more heteroatoms from the group (O, N, S), a keto group or a —SO$_2$— group and which groups may be substituted with a hydroxy or amino group, or R$_5$ and R$_6$ independently of each other represent a C$_{3-8}$ cycloalkyl group or C$_{3-8}$ cycloalkenyl group which may contain one or more ring heteroatoms from the group (O, N, S) or the —SO$_2$— group and which groups may be substituted with a hydroxy group, alkyl (C$_{1-3}$), the —SO$_2$— group, the keto group, amino group, monoalkylamino group (C$_{1-3}$) or dialkylamino group (C$_{1-3}$), or R$_5$ represents a naphtyl group or a phenyl group which phenyl group may be substituted with 1, 2 or 3 substituents Y wherein Y has the meaning as described hereinabove, with the proviso that R$_6$ represents a hydrogen atom, or a branched or unbranched alkyl group (C$_{1-5}$) which alkyl group may contain one or more heteroatoms from the group (O, N, S) or the —SO$_2$— group and which alkyl group may be substituted with a hydroxy, keto or amino group, or R$_5$ and R$_6$— together with the nitrogen atom to which they are bonded—form a monocyclic, bicyclic or tricyclic alkyl or alkenyl group which may contain ring heteroatoms from the group (O, N, S), the keto or the SO$_2$ group and which monocyclic, bicyclic or tricyclic alkyl or alkenyl group may be substituted with a hydroxy group, alkyl (C$_{1-3}$) group, SO$_2$ group, keto group, amino group, monoalkylamino group (C$_{1-3}$), dialkylamino group (C$_{1-3}$), pyrrolidinyl group or piperidinyl group, which monocyclic, bicyclic or tricyclic alkyl or alkenyl group may contain an annelated phenyl group which annelated phenyl group may be substituted with 1 or 2 substituents Y, wherein Y has the meaning as described herein above, R$_7$ represents branched or unbranched C$_{1-3}$alkyl.

At least one centre of chirality is present (at the C$_4$ position of the 4,5-dihydro-1H-pyrazole moiety) in the compounds of the formula (Ia) and (Ib). The invention relates both to racemates, mixtures of diastereomers and the individual stereoisomers of the compounds having formula (Ia) or (Ib). Particular compounds of interest of formula (Ia) or (Ib) have the absolute stereoconfiguration at the C$_4$ position of the 4,5-dihydro-1H-pyrazole moiety as represented by the formulas (1a*) and (1b*):

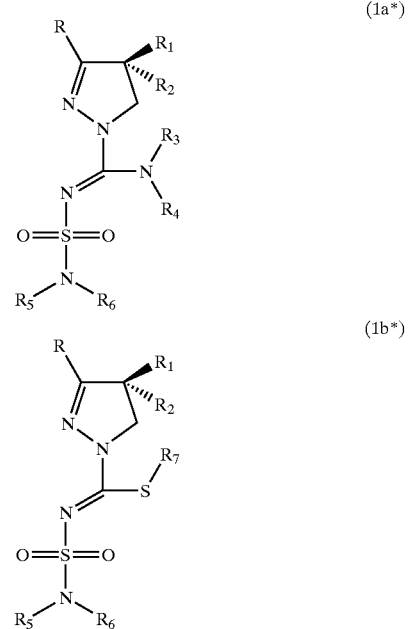

The invention also relates both to the E isomer, Z isomer and E/Z mixtures of compounds having formula (Ia) or (Ib).

The compounds of the invention can be brought into forms suitable for administration by means of usual processes using auxiliary substances and/or liquid or solid carrier materials.

Due to the potent CB$_1$ antagonistic activity the compounds according to the invention are suitable for use in the treatment of psychiatric disorders such as psychosis, anxiety, depression, attention deficits, memory disorders, cognitive disorders, appetite disorders, obesity, addiction, appetence, drug dependence and neurological disorders such as neurodegenerative disorders, dementia, dystonia, muscle spasticity, tremor, epilepsy, multiple sclerosis, traumatic brain injury, stroke, Parkinson's disease, Alzheimer's disease, epilepsy, Huntington's disease, Tourette's syndrome, cerebral ischaemia, cerebral apoplexy, craniocerebral trauma, stroke, spinal cord injury, neuroinflammatory disorders, plaque sclerosis, viral encephalitis, demyelinisation related disorders, as well as for the treatment of pain disorders, including neuropathic pain disorders, and other diseases involving cannabinoid neurotransmission, including the treatment of septic shock, glaucoma, cancer, diabetes, emesis, nausea, asthma, respiratory diseases, gastrointestinal disorders, gastric ulcers, diarrhoea and cardiovascular disorders.

The affinity of the compounds of the invention for cannabinoid CB$_1$ receptors was determined using membrane preparations of Chinese hamster ovary (CHO) cells in which the human cannabinoid $CB_1$ receptor is stably transfected in conjunction with [$^3$H]CP-55,940 as radioligand. After incubation of a freshly prepared cell membrane preparation with the [$^3$H]-ligand, with or without addition of compounds of the invention, separation of bound and free ligand was performed by filtration over glassfiber filters. Radioactivity on the filter was measured by liquid scintillation counting.

The cannabinoid $CB_1$ antagonistic activity of compounds of the invention was determined by functional studies using CHO cells in which human cannabinoid $CB_1$ receptors are stably expressed. Adenylyl cyclase was stimulated using forskolin and measured by quantifying the amount of accumulated cyclic AMP. Concomitant activation of $CB_1$ receptors by $CB_1$ receptor agonists (e.g. CP-55,940 or (R)-WIN-55,212-2) can attenuate the forskolin-induced accumulation of cAMP in a concentration-dependent manner. This $CB_1$ receptor-mediated response can be antagonised by $CB_1$ receptor antagonists such as the compounds of the invention.

Intermediates having formula (II) (see below) can be obtained according to methods known, for example: a) Francotte, E.; Tong, Z. *Chem. Abstr.* 126, 213598; b) Rempfler, H. and Kunz, W. *Chem. Abstr.* 113, 40432; c) Rempfler, H. and Kunz, W. *Chem. Abstr.* 107, 217473.

Intermediates having formula (III) wherein $R_2$ represents hydrogen (see below) can be obtained according to methods known, for example: a) EP 0021506; b) DE 2529689, c) Grosscurt, A. C. et al., *J. Agric. Food Chem.* 1979, 27, (2), 406.

Intermediates having formula (III) wherein $R_2$ represents a hydroxy group can be obtained by reacting a compound having formula (II) with hydrazine or hydrazine hydrate

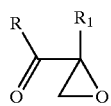
(II)

This reaction, preferably carried out in an organic solvent such as ethanol, yields a compound having formula (III) wherein $R_2$ represents a hydroxy group.

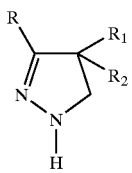
(III)

Suitable synthetic routes for the compounds of the invention are the following:

Synthetic Route A

Step 1: Reaction of a Compound Having Formula (III)

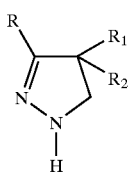
(III)

with a compound having formula (IV).

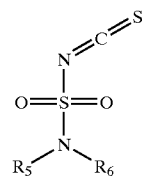
(IV)

This reaction is preferably carried out in an organic solvent, such as for example dichloromethane, and yields a compound having formula (V) wherein R, $R_1$, $R_2$, $R_5$ and $R_6$ have the meaning as described above for compound (Ia), and which are new.

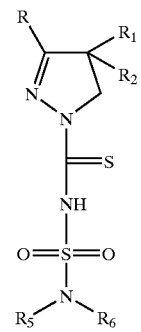
(V)

Step 2: reaction of a compound having formula (V) with a compound $R_7$-X, wherein X represents a leaving group, for example an iodide group, and $R_7$ has the meaning as described above for (Ib) gives a compound having formula (Ib).

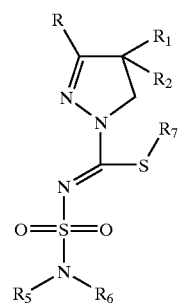
(Ib)

This reaction is preferably carried out in the presence of a base, for example triethylamine.

Step 3: reaction of a compound having formula (Ib) with an amine having formula $HNR_3R_4$ wherein $R_3$ and $R_4$ have the meanings as described above, analogous to the method described in *Synth. Commun.* 1996, 26, (23), 4299. This reaction gives a compound having formula (Ia).

Synthetic Route A1

Step 1: Reaction of a Compound Having Formula (V)

(V)

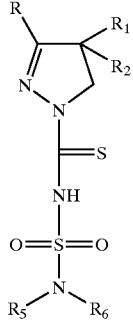

with an amine having formula $HNR_3R_4$ wherein $R_3$ and $R_4$ have the meanings as described above in the presence of a mercury(II) salt, for example $HgCl_2$, gives a compound having formula (Ia).

This reaction is preferably carried out in an organic solvent, such as for example acetonitrile, analogous to the method described in *Synth. Commun.* 1996, 26, (23), 4299.

Synthetic Route A2

Step 1: Reaction of a Compound Having Formula (III)

(III)

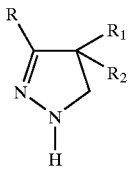

with a isocyanate derivative having formula (VI), followed by treatment with an amine $HNR_5R_6$ (VI)

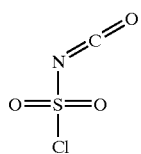

This reaction is preferably carried out in an organic solvent like dichloromethane, and yields a compound having formula (VII). Compounds having formula (VII) wherein R, $R_1$, $R_2$, $R_5$ and $R_6$ have the meaning as described herein above for compound (Ia) are new.

(VII)

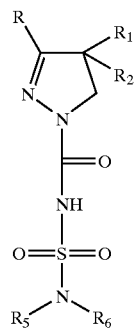

Step 2: reaction of a compound having formula (VII) with a halogenating agent, such as for example $PCl_5$, gives a compound having formula (VIII)

(VIII)

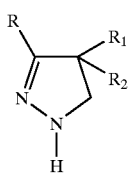

wherein $R_{10}$ represents a halogen atom, for example a chloro atom. This reaction is preferably carried out in an organic solvent such as chlorobenzene. Compounds having formula (VIII) wherein R, $R_1$, $R_2$, $R_5$ and $R_6$ have the meanings as described above for compound (Ia) and wherein $R_{10}$ represents a halogen atom, are new.

Step 3: reaction, preferably carried out in an inert organic solvent such as dichloromethane, of a compound having formula (VIII) with an amine having formula $HNR_3R_4$ wherein $R_3$ and $R_4$ have the meanings as described above gives a compound having formula (Ia).

Synthetic Route A3

Step 1: reaction of a compound having formula (III)

(III)

with a compound having formula (IX)

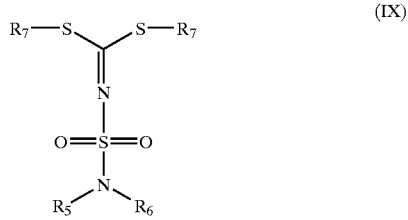

gives a compound having formula (Ib), (see e.g. *Chem. Ber.* 1966, 99, 2885 and *Chem. Ztg.* 1984, 108, (12), 404).

The preparation of the compounds is illustrated in the following examples.

EXAMPLE 1

3-(4-Chlorophenyl)-N'-(((ethyl)propylamino) sulfonyl)-N-methyl-4-phenyl-4,5-dihydro-1H-pyrazole-1-carboxamidine Part A: To a stirred solution of ((ethyl)propylamino) sulfonyl isothiocyanate (5.98 gram, 25.4 mmol) in dry dichloromethane in a nitrogen atmosphere is added of 3-(4-chlorophenyl)-4-phenyl-4,5-dihydro-1H-pyrazole (6.52 gram, 25.4 mmol). After stirring for 90 minutes the resulting solution is concentrated in vacuo and purified by column chromatography ($CH_2Cl_2$, silicagel, $R_f$~0.45). The resulting solid is recrystallized from diethyl ether to give 3-(4-chlorophenyl)-N-(((ethyl)propylamino)sulfonyl)-4-phenyl-4,5-dihydro-1H-pyrazole-1-thiocarboxamide (6.57 gram, 56% yield). Melting point: 144–146° C.

Part B: To a stirred suspension of 3-(4-chlorophenyl)-N-(((ethyl)propylamino)sulfonyl)-4-phenyl-4,5-dihydro-1H-pyrazole-1-thiocarboxamide (2.32 gram, 5 mmol) in acetonitrile (20 mL) is added cold methylamine (4 mL). To the resulting solution is added a solution of $HgCl_2$ (1.5 gram) in acetonitrile (10 mL). The resulting black suspension is stirred for four hours. The precipitate is removed by filtration. The filtrate is concentrated in vacuo, dissolved in dichloromethane and successively washed with aqueous 0.5 N NaOH solution and water, dried over $Na_2SO_4$, filtered and concentrated in vacuo. The resulting oil is crystallized from diethyl ether to give 3-(4-chlorophenyl)-N'-(((ethyl) propylamino)sulfonyl)-N-methyl-4-phenyl-4,5-dihydro-1H-pyrazole-1-carboxamide (1.78 gram, 77% yield). Melting point (MP):129–131° C.

In an analogous manner the compounds having formula (Ia) listed below have been prepared:

2. 3-(4-Chlorophenyl)-N'-(((ethyl)methylamino) sulfonyl)-N-methyl-4-phenyl-4,5-dihydro-1H-pyrazole-1-carboxamidine. MP: 112–115° C.

3. 3-(4-Chlorophenyl)-N'-((diethylamino)sulfonyl)-N-(2-hydroxyethyl)-4-phenyl-4,5-dihydro-1H-pyrazole-1-carboxamidine. MP: 104–106° C.

4. 3-(4-Chlorophenyl)-N-(2-hydroxyethyl)-N'-((piperidin-1-yl)sulfonyl)-4-phenyl-4,5-dihydro-1H-pyrazole-1-carboxamidine. MS (ESI+): 490 ($MH^+$).

5. 3-(4-Chlorophenyl)-N'-((diethylamino)sulfonyl)-N-(2-(morpholin-4-yl)ethyl)-4-phenyl-4,5-dihydro-1H-pyrazole-1-carboxamidine. MS (ESI+): 547 ($MH^+$))

6. 3-(4-Chlorophenyl)-N'-((dimethylamino)sulfonyl)-N-(2-(morpholin-4-yl)ethyl)-4-phenyl-4,5-dihydro-1H-pyrazole-1-carboxamide. Amorphous.

7. 3-(4-Chlorophenyl)-N'-((diethylamino)sulfonyl)-N-(2-(dimethylamino)ethyl)-4-phenyl-4,5-dihydro-1H-pyrazole-1-carboxamide. MS(ESI+): 505 ($MH^+$)).

8. 3-(4-Chlorophenyl)-N-(3-(dimethylamino)propyl)-N'-((dimethylamino)sulfo-nyl)-4-phenyl-4,5-dihydro-1H-pyrazole-1-carboxamide. Amorphous.

9. 3-(4-Chlorophenyl)-N-(2-(piperidin-1-yl)ethyl)-N'-((piperidin-1-yl)sulfonyl)-4-phenyl-4,5-dihydro-1H-pyrazole-1-carboxamide. MS (ESI+): 557 ($MH^+$)).

10. 3-(4-Chlorophenyl)-N-(2-(morfolin-4-yl)ethyl)-N'-((piperidin-1-yl)sulfonyl)-4-phenyl-4,5-dihydro-1H-pyrazole-1-carboxamide. MS (ESI+): 559 ($MH^+$)); MP: 174–176° C.

11. 3-(4-Chlorophenyl)-N-(2-(dimethylamino)ethyl)-N'-((dimethylamino)sulfo-nyl)-4-phenyl-4,5-dihydro-1H-pyrazole-1-carboxamide. Amorphous.

12. 3-(4-Chlorophenyl)-N-(2-(diethylamino)ethyl)-N'-((dimethylamino)sulfonyl)-4-phenyl-4,5-dihydro-1H-pyrazole-1-carboxamide. Amorphous.

13. 3-(4-Chlorophenyl)-N-(3-(dimethylamino)propyl)-N'-((diethylamino)sulfo-nyl)-4-phenyl-4,5-dihydro-1H-pyrazole-1-carboxamide.MS(ESI+): 519 ($MH^+$).

14. 3-(4-Chlorophenyl)-N-(2-(diethylamino)ethyl)-N'-((diethylamino)sulfonyl)-4-phenyl-4,5-dihydro-1H-pyrazole-1-carboxamide. MP: 182–185° C.

15. 3-(4-Chlorophenyl)-N-(2-(dimethylamino)ethyl)-N'-((piperidin-1-yl)sulfonyl)-4-phenyl-4,5-dihydro-1H-pyrazole-1-carboxamide. Amorphous.

16. 3-(4-Chlorophenyl)-N-(2-(diethylamino)ethyl)-N'-((pyrrolidin-1-yl)sulfonyl)-4-phenyl-4,5-dihydro-1H-pyrazole-1-carboxamide. Amorphous.

17. 3-(4-Chlorophenyl)-N'-((diethylamino)sulfonyl)-N-(1-methylpiperidin-4-yl)-4-phenyl-4,5-dihydro-1H-pyrazole-1-carboxamide. Amorphous.

18. 3-(4-Chlorophenyl)-N'-((dimethylamino)sulfonyl)-N-(2-hydroxyethyl-4-phenyl-4,5-dihydro-1H-pyrazole-1-carboxamide. MP: 123–126° C.

19. 3-(4-Chlorophenyl)-N'-((diethylamino)sulfonyl)-N-methyl-4-phenyl-4,5-dihydro-1H-pyrazole-1-carboxamidine. Amorphous. $R_f$~0.4 (diethyl ether).

20. 3-(4-Chlorophenyl)-N'-(((ethyl)propylamino) sulfonyl)-N-Methyl-4-phenyl-4,5-dihydro-1H-pyrazole-1-carboxamidine. MP: 129–131° C.

21. 3-(4-Chlorophenyl)-N-methyl-N'-((pyrrolidin-1-yl) sulfonyl)-4-phenyl-4,5-dihydro-1H-pyrazole-1-carboxamidine. Amorphous. $R_f$~0.3 (MTBE).

22. 3-(4-Chlorophenyl)-N-methyl-N'-(((methyl) propylamino)sulfonyl)-4-phenyl-4,5-dihydro-1H-pyrazole-1-carboxamindine. MP: 132–134° C.

23. 3-(4-Chlorophenyl)-N,N-dimethyl-N'-((pyrrolidin-1-yl)sulfonyl)-4-phenyl4,5-dihydro-1H-pyrazole-1-carboxamiidine. Amorphous. $R_f$~0.25 (MTBE).

24. 3-(4-Chlorophenyl)-N-methyl-N'-((piperidin-1-yl) sulfonyl)-4-phenyl-4,5-dihydro-1H-pyrazole-1-carboxamidine. MP: 175–177° C.

25. 3-(4-Chlorophenyl)-N'-((hexahydro-1H-azepin-1-yl) sulfonyl)-N-methyl-4-phenyl-4,5-dihydro-1H-pyrazole-1-carboxamide. Amorphous.

26. 3-(4-Chlorophenyl)-N'-((dipropylamino)sulfonyl)-N-methyl-4-phenyl-4,5-dihydro-1H-pyrazole-1-carboxamide. MP: 141–142° C.

27. 3-(4-Chlorophenyl)-N'-(((isopropyl)methylamino) sulfonyl)-N-methyl-4-phenyl-4,5-dihydro-1H-pyrazole-1-carboxamide. MP: 134–136° C.

28. 3-(4-Chlorophenyl)-N-methyl-N'-((octahydroazocin-1-yl)sulfonyl)-4-phenyl-4,5-dihydro-1H-pyrazole-1-carboxoamidine. MP: 165–168° C.

29. 3-(4-Chlorophenyl)-N-ethyl-N'-((piperidin-1-yl)sulfonyl)-4-phenyl-4,5-dihydro-1H-pyrazole-1-carboxamidine. Amorphous.

30. 3-(4-Chlorophenyl)-N'-((dimethylamino)sulfonyl)-N-methyl-4-phenyl-4,5-dihydro-1H-pyrazole-1-carboxamidine. MP: 166–168° C.

EXAMPLE 31

3-(4-Chlorophenyl)-N'-((dimethylamino)sulfonyl)-N-propyl-4-phenyl-4,5-dihydro-1H-pyrazole-1-carboxamidine Part A: To a stirred solution of chlorosulfonyl isocyanate (1.73 mL, 20 mmol) in dry dichloromethane (20 mL) is very slowly added a solution of 3-(4-chlorophenyl)-4-phenyl-4,5-dihydro-1H-pyrazole (5.13 gram, 20 mmol) in dry dichloromethane (125 mL) at −5° C. After stirring for 30 minutes the reaction mixture is allowed to attain room temperature and stirred for another 2 hours. After cooling to 0° C. liquid dimethylamine (5 mL) is added and the resulting solution is stirred for another hour at 0° C. and for 2 hours at room temperature. The solution is washed with water, filtered over hyflo and concentrated in vacuo. Flash chromatography (MTBE, $R_f$~0.3) gives 3-(4-chlorophenyl)-N-((dimethylamino)sulfonyl)-4-phenyl-4,5-dihydro-1H-pyrazole-1-carboxamide (4.75 g, 58%). MP: 210–212° C.

Part B: A mixture of 3-(4-chlorophenyl)-N-((dimethylamino)sulfonyl)-4-phenyl-4,5-dihydro-1H-pyrazole-1-carboxamidie (1.47 gram, 3.62 mmol) and phosphorus pentachloride (0.80 gram, 3.84 mmol) in chlorobenzene (20 mL) is heated at reflux temperature for 1 hour. After thorough concentration in vacuo, the formed 3-(4-chlorophenyl)-N-((dimethylamino)sulfonyl)-4-phenyl-4,5-dihydro-1H-pyrazole-1-carboximidoyl chloride is suspended in dry dichloromethane and reacted with cold n-propylamine (1.0 mL) at 0° C. After stirring for 1 hour, the mixture is dissolved in ethyl acetate and washed with water and concentrated in vacuo. The residue is purified by column chromatography (dichloromethane/acetone=19/1 (v/v), $R_f$~0.35) to give an oil (0.82 g). Crystallisation from diethyl ether, followed by recrystallisation from ethanol gives 3-(4-chlorophenyl)-N'-((dimethylamino)sulfonyl)-N-propyl-4-phenyl-4,5-dihydro-1H-pyrazole-1-carboxamidine (0.38 gram, 23% yield). MP: 127–129° C.

In an analogous manner the compounds having formula (Ia) listed below have been prepared:

32. 3-(4-Chlorophenyl)-N'-((dimethylamino)sulfonyl)-N-(2-fluoroethyl)-4-phenyl-4,5-dihydro-1H-pyrazole-1-carboxamidine. MP: 128–131° C.

33. 3-(4-Chlorophenyl)-N'-((dimethylamino)sulfonyl)-4-phenyl-N-(2,2,2-trifluoroethyl)-4,5-dihydro-1H-pyrazole-1-carboxamide. MP: 158–159° C.

34. 3-(4Chlorophenyl)-N'-((dimethylamino)sulfonyl)-N-methoxy-4-phenyl-4,5-dihydro-1H-pyrazole-1-carboxamidine. MP: 170–172° C.

EXAMPLE 35

3-(4-Chlorophenyl)-N-((piperidin-1-yl)sulfonyl)-4-phenyl-4,5-dihydro-1H-pyrazole-1-carboximidothiolic acid methyl ester Part A: To a stirred solution of (piperidin-1-yl)sulfonyl isothiocyanate (54.77 g, 266 mmol) in dry dichloromethane (900 mL) in a nitrogen atmosphere is added 3-(4-chlorophenyl)-4-phenyl-4,5-dihydro-1H-pyrazole (68.3 gram, 266 mmol). After stirring for 16 hours an additional amount of dichloromethane is added. The resulting solution is twice washed with water, dried over $Na_2SO_4$, and concentrated in vacuo. After addition of MTBE, the residue crystallizes. The crystalline material is collected and washed with MTBE to give 3-(4-chlorophenyl)-4-phenyl-N-((piperidin-1-yl)sulfonyl)-4,5-dihydro-1H-pyrazole-1-carboxamidine (77.6 gram, 63% yield).

Part B: To a stirred solution of 3-(4-chlorophenyl)-4-phenyl-N-((piperidin-1-yl)sulfonyl)-4,5-dihydro-1H-pyrazole-1-thiocarboxamide (30 gram, 64.9 mmol) in acetone (1 L) is added triethylamine (18.0 mL, 130 mmol). To the resulting yellow solution is added methyl iodide (9.12 g, 64 mmol) and the resulting solution is stirred for 16 hours at room temperature. The formed precipitate is removed by filtration. The filtrate is washed with water, concentrated in vacuo to give a yellow solid. Recrystallisation from MTBE gives 3-(4-chlorophenyl)-N-((piperidin-1-yl)sulfonyl)-4-phenyl-4,5-dihydro-1H-pyrazole-1-carboxamidothioic acid methyl ester (27.9 gram, 90% yield). MP: 192–194° C.

In an analogous manner the compounds having formula (Ib) listed below have been prepared:

36. 3-(4-Chlorophenyl)-N-((dimethylamino)sulfonyl)-4-phenyl-4,5-dihydro-1H-pyrazole-1-carboximidothioic acid methyl ester. MP: 159–160° C.

37. 3-(4-Chlorophenyl)-N-((diethylamino)sulfonyl)-4-phenyl-4,5-dihydro-1H-pyrazole-1-carboximidothioic acid methyl ester. MP: 141–143° C.

38. 3-(4-Chlorophenyl)-4-phenyl-N-((1,2,3,4-tetrahydroisoquinolin-2-yl)sulfonyl)-4,5-dihydro-1H-pyrazole-1-carboxamidothioic acid methyl ester. MP: 143-145° C.

39. 3-(4-Chlorophenyl)-N-(((ethyl)phenylamino)sulfonyl)-4-phenyl-4,5-dihydro-1H-pyrazole-1-carboximidothioic acid methyl ester. MP: 143–146° C.

40. 3-(4-Chlorophenyl)-N-((diethylamino)sulfonyl)-4-hydroxy-4-phenyl-4,5-dihydro-1H-pyrazole-1-caroximidothioic acid methyl ester. Amorphous.

41. 3-(4-Chlorophenyl)-N-((diethylamino)sulfonyl)-4-(pyridin-4-yl)-4,5-dihydro-1H-pyrazole-1-carboximidothioic acid methyl ester. Amorphous.

42. 3-(4-Chlorophenyl)-N-((piperidin-1-yl)sulfonyl)-4-(3-(trifluoromethyl)phenyl)-4,5-dihydro-1H-pyrazole-1-carboximidothioic acid methyl ester. Amorphous.

43. 3-(4-Chlorophenyl)-N-((dimethylamino)sulfonyl)-4-(3-(trifluoromethyl)phenyl)-4,5-dihydro-1H-pyrazole-1-carboximidothioic acid methyl ester. Amorphous.

44. 3-(4-Chlorophenyl)-N-(((ethyl)methylamino)sulfonyl)-4-(pyridin-3-yl)-4,5-dihydro-1H-pyrazole-1H-pyrazole-1-carboximidothioic acid methyl ester.MP: 133–136° C.

45. 3-(4-Chlorophenyl)-N-((piperidin-1-yl)sulfonyl)-4-(pyridin-3-yl)-4,5-dihydro-1H-pyrazole-1-pyrazole-1-carboximidothioic acid methyl ester. MP: 182–185° C.

46. 3-(4-Chlorophenyl)-N-((morpholin-4-yl)sulfonyl)-4-phenyl-4,5-dihydro-1H-pyrazole-1-carboximidothioic acid methyl ester. MP: 202–204° C.

47. 3-(4-Chlorophenyl)-4-(2-fluorophenyl)-N-((morpholin-4-yl)sulfonyl)-4,5-dihydro-1H-pyrazole-1-carboximidothioic acid methyl ester. MP:205–207° C.

48. 3-(4-Chlorophenyl)-4-(2-fluorophenyl)-N-((piperidin-1-yl)sulfonyl)-4,5-dihydro-1H-pyrazole-1-carboximidothioic acid methyl ester. MP:196–198° C.

49. 3-(4-Chlorophenyl)-4-(2-fluorophenyl)-N-((dimethylamino)sulfonyl)-4,5-dihydro-1H-pyrazole-1-carboximidothioic acid methyl ester. MP:181–183° C.

50. 3-(4-Chlorophenyl)-4-(2,6-difluorophenyl)-N-((morpholin-4-yl)sulfonyl)-4,5-dihydro-1H-pyrazole-1-carboximidothioic acid methyl ester. MP:231–233° C.

51. 3-(4-Chlorophenyl)-4-(2,6-difluorophenyl)-N-((piperidin-1-yl)sulfonyl)-4,5-dihydro-1H-pyrazole-1-carboximidothioic acid methyl ester. MP:221–225° C.

52. 3-(4-Chlorophenyl)-4-(2,6-difluorophenyl)-N-((dimethylamino)sulfonyl)-4,5-dihydro-1H-pyrazole-1-carboximidothioic acid methyl ester. MP:181–185° C.

53. 3-(4-Chlorophenyl)-N-((1,1-dioxidothiomorpholin-4-yl)sulfonyl)-4-phenyl-4,5-dihydro-1H-pyrazol-1-carboximidothioic acid methyl ester. MP: 216–217° C.

54. 3-(5-Chlorothien-2-yl)-N-((diethylamino)sulfonyl)-4-phenyl-4,5-dihydro-1H-pyrazole-1-carboximidothioic acid methyl ester. Amorphous.

EXAMPLE 55

3-(4-Chlorophenyl)-N-methyl-4-phenyl-N'-((piperidin-1-yl)sulfonyl)-4,5-dihydro-1H-pyrazole-1-carboxamidine To a cooled mixture (<0° C.) of 3-(4-chlorophenyl)-N-((piperidin-1-yl)sulfonyl)-4-phenyl-4,5-dihydro-1H-pyrazole-1-carboxamidothioic acid methyl ester (10.0 gram, 21 mmol) in methanol (75 mL) is added cold methylamine (15 mL). The resulting mixture is allowed to attain room temperature and stirred for 3 hours at 50° C. After cooling to room temperature the mixture is concentrated in vacuo, dissolved in dichloromethane, washed twice with water, dried over Na$_2$SO$_4$, filtered and concentrated in vacuo. Subsequent flash chromatography (EtOAc/MeOH/NH$_4$OH (25% aq.)=95/5/0.5 (v/v)), followed by recrystallisation from diisopropyl ether gives 3-(4-chlorophenyl)-N-methyl-4-phenyl-N'-((piperidin-1-yl)sulfonyl)-4,5-dihydro-1H-pyrazole-1-carboxamidine (7.87 gram, 81% yield) as a white solid. MP: 175–177° C.

In an analogous manner the compounds having formula (Ia) listed below—including those in table 1—have been prepared:

56. 3-(4-Chlorophenyl)-N-cyclopropyl-4-phenyl-N'-((piperidin-1-yl)sulfonyl)-4,5-dihydro-1H-pyrazole-1-carboxamidine. MP: 142–144° C.

57. 3-(4-Chlorophenyl)-N'-((diethylamino)sulfonyl)-N-methyl-4-hydroxy-4-phenyl-4,5-dihydro-1H-pyrazol-1-carboxamide. MP: 180–182° C.

58. 3-(5-Chlorothien-2-yl)-N'-((diethylamino)sulfonyl)-N-methyl-4-phenyl-4,5-dihydro-1H-pyrazole-1-carboxamide. MP: 122–123° C.

59. 3-(4-Chlorophenyl)-N'-((dimethylamino)sulfonyl)-N-isopropyl-4-phenyl-4,5-dihydro-1H-pyrazole-1-carboxamidine. MP: 169–170° C.

60. 3-(4-Chlorophenyl)-N'-((dimethylamino)sulfonyl)-N-(1-methylpiperidin-4-yl)-4-phenyl-4,5-dihydro-1H-pyrazole-1-carboxamidine. MP: 144–146° C.

61. 3-(4-Chlorophenyl)-N-cyclopropyl-N'-((diethylamino)sulfonyl)-4-phenyl-4,5-dihydro-1H-pyrazole-1-carboxamidine. MP: 150–151° C.

62. 3-(4-Chlorophenyl)-N'-((diethylamino)sulfonyl)-N-ethyl-4-phenyl-4,5-dihydro-1H-pyrazole-1-carboxamidine. MP: 116–119° C.

63. 3-(4-Chlorophenyl)-N'-((diethylamino)sulfonyl)-N,N-dimethyl-4-hydroxy-4-phenyl-4,5-dihydro-1H-pyrazole-1-carboxamidine. MP: 135–137° C.

64. N'-((Diethylamino)sufonyl)-N,N-dimethyl-3-(4-fluorophenyl)-4-phenyl-4,5-dihydro-1H-pyrazole-1-carboxamidine. MP: 159–160° C.

65. 3-(4-Chlorophenyl)-N'-((diethylamino)sulfonyl)-N-isopropyl-4-phenyl-4,5-dihydro-1H-pyrazole-1-carboxamidine. MP: 81–85° C.

66. 3-(4-Chlorophenyl)-N'-((dimethylamino)sulfonyl)-N-ethyl,N-methyl-4-phenyl-4,5-dihydro-1H-pyrazole-1-carboxamidine. Amorphous.

67. 3-(4-Chlorophenyl)-N-ethyl,N-methyl-N'-((piperidin-1-yl)sulfonyl)-4-phenyl-4,5-dihydro-1H-pyrazol-1-carboxamidine. MP: 178° C.

68. 3-(4-Chlorophenyl)-N'-((diethylamino)sulfonyl)-N-ethyl-4-hydroxy-4-phenyl-4,5-dihydro-1H-pyrazole-1-carboxamidine. MP: 162–165° C.

69. 3-(4-Chlorophenyl)-N-methyl-N'-((1,2,3,4-tetrahydroisoquinolin-2-yl)sulfo-nyl)-4-phenyl-4,5-dihydro-1H-pyrazole-1-carboxamidine. Amorphous.

70. 3-(4-Chlorophenyl)-N'-(((ethyl)phenylamino)sulfonyl)-N-methyl-4-phenyl-4,5-dihydro-1H-pyrazole-1-carboxamidine. MP: 145–147° C.

71. N'-((Diethylamino)sufonyl)-3-(4-chlorophenyl)-N-methyl-4-(pyridin-4-yl)-4,5-dihydro-1H-pyrazole-1-carboxamidine. MP: 109–111° C.

72. 3-(4-Chlorophenyl)-N'-((dimethylamino)sulfonyl)-N-methyl-4-(pyridin-3-yl)-4,5-dihydro-1H-pyrazole-1-carboxamidine. MP: 157–159° C.

73. 3-(4-Chlorophenyl)-N'-((diethylamino)sulfonyl)-N-methyl-4-(pyridin-3-yl)-4,5-dihydro-1H-pyrazole-1carboxaimdine. MP: 85–89° C.

74. 3-(4-Chlorophenyl)-N'-((dimethylamino)sulfonyl)-N-methyl-4-(pyridin-4-yl)-4,5-dihydro-1H-pyrazole-1-carboxamidine. MP: 178–182° C.

75. 3-(4-Chlorophenyl)-N-methyl-N'-((piperidin-1-yl)sulfonyl)-4-(3-(trifluoromethyl)phenyl)-4,5-dihydro-1H-pyrazole-1-carboxamidine. MP: 168–170° C.

76. 3-(4-Chlorophenyl)-N'-((dimethylamino)sulfonyl)-N-methyl-4-(3-(trifluoromethyl)phenyl)-4,5-dihydro-1H-pyrazole-1-carboxamidine. MP: 65–68° C.

77. 3-(4-Chlorophenyl)-N'-(((ethyl)methylamino)sulfonyl)-N-methyl-4-(pyridin-3-yl)-4,5-dihydro-1H-pyrazole-1-carboxamidine. MP: 125–128° C.

78. 3-(4-Chlorophenyl)-N-methyl-N'-((piperidin-1-yl)sulfonyl)-4-(pyridin-3-yl)-4,5-dihydro-1H-pyrazole-1-carboxamidine. MP: 174–177° C.

79. 3-(4-Chlorophenyl)-4-(2,6-difluorophenyl)-N-methyl-N'-((morpholin-4-yl)sulfonyl)-4,5-dihydro-1H-pyrazole-1carboxamidine. MP: 223–235° C.

80. 3-(4-Chlorophenyl)-4-(2,6-difluorophenyl)-N'-((dimethylamino)sulfonyl)-N-methyl-4,5-dihydro-1H-pyrazole-1-carboxamidine. MP: 214–216° C.

81. 3-(4-Chlorophenyl)-4-(2,6-difluorophenyl)-N-methyl-N'-((piperidin-1-yl)sulfonyl)-4,5-dihydro-1H-pyrazole-1-carboxamidine. MP: 260–263° C.

82. 3-(4-Chlorophenyl)-4-(3-fluorophenyl)-N-methyl-N'-((piperidin-1-yl)sulfonyl)-4,5-dihydro-1H-pyrazole-1carboxamidine. MP: 170° C.

83. 3-(4-Chlorophenyl)-4-(2-fluorophenyl)-N-methyl-N'-((piperidin-1-yl)sulfonyl)-4,5-dihydro-1H-pyrazole-1-carboxamidine. MP: 223–225° C.

84. 3-(4-Chlorophenyl)-N'-((dimethylamino)sulfonyl)-4-(2-fluorophenyl)-N-methyl-4,5-dihydro-1H-pyrazole-1-carboxamidine. MP: 173–175° C.

85. 3-(4-Chlorophenyl)-N'-((dimethylamino)sulfonyl)-4-(3-fluorophenyl)-N-methyl-4,5-dihydro-1H-pyrazole-1-carboxamidine. MP: 110° C.

86. 3-(4-Chlorophenyl)-4-(2-fluorophenyl)-N-methyl-N'-((morpholin-4-yl)sulfonyl)-4,5-dihydro-1H-pyrazole-1carboxamidine. MP: 165–168° C.

87. 3-(4-Chlorophenyl)-N'-((1,1-dioxidothiomorpholin-4-yl)sulfonyl)-N-methyl-4-phenyl-4,5-dihydro-1H-pyrazole-1-carboxamidine. MP: 268–271° C.

88. 3-(4-Chlorophenyl)-N'-((4-hydroxypiperidin-1-yl)sulfonyl)-N-methyl-4-phenyl-4,5-dihydro-1H-pyrazole-1-carboxamidine. MP: 80° C.

97. 3-(4-Chlorophenyl)-N-(([1,4']bipiperidin-1'-yl)sulfonyl)-4-phenyl-4,5-dihydro-1H-pyrazole-1-carboximidothioic acid methyl ester. MP: 245° C.

98. 3-(4-Chlorophenyl)-N-(((1-methylpiperidin-4-yl)methylamino)sulfonyl)-4-phenyl-4,5-dihydro-1H-pyrazole-1-carboximidothioic acid methyl ester. Oil. $R_f$~0.15 (methanol/dichloromethane=5/95 (v/v)).

99. 3-(4-Chlorophenyl)-N-((4-methyl-1,4-diazepan-1-yl)sulfonyl)-4-phenyl-4,5-dihydro-1H-pyrazole-1-carboximidothioic acid ethyl ester. Amorphous. $R_f$~0.10 (methanol/dichloromethane=5/95 (v/v)).

TABLE 1

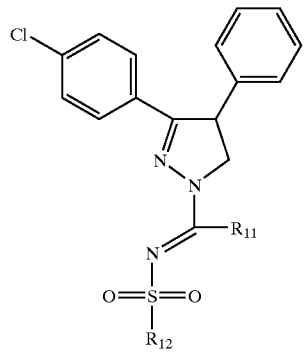

| Example: | $R_{11}$ | $R_{12}$ | MP (° C.) | Salt form |
|---|---|---|---|---|
| 89: | 4-Methyl-1,4-diazepan-1-yl | Dimethylamino | 197–200 | 0.5 Fumarate |
| 90: | 1,4-Diazepan-1-yl | Piperidin-1-yl | Amorphous | |
| 91: | 1,4-Diazepan-1-yl | Dimethylamino | Amorphous | |
| 92: | 4-Methyl-1,4-diazepan-1-yl | Piperidin-1-yl | 159–164 | |
| 93: | 4-Methylpiperazin-1-yl | Dimethylamino | 191–193 | |

EXAMPLE 94

3-(4-Chlorophenyl)-N(4-methylpiperazin-1-yl)sulfonyl)-4-phenyl-4,5-dihydro-1H-pyrazole-1-carboximidothioic acid methyl ester Part A: A stirred mixture of 3-(4-chlorophenyl)-4-phenyl4,5-dihydro-1H-pyrazole (3.21 gram, 11.3 mmol), [(4-methylpiperazin-1-yl)sulfonyl]dithioimido-carbonic acid dimethyl ester (3.08 gram, 12.0 mmol) and pyridine (25 mL) is heated at 100° C. for 24 hours in a nitrogen atmosphere. After cooling to room temperature the mixture is concentrated in vacuo, water is added and the resulting mixture is extracted with dichloromethane. The dichloromethane extract is washed twice with water, dried over $Na_2SO_4$, filtered and concentrated in vacuo. Subsequent flash chromatographic purification gives 3-(4-chlorophenyl)-N-((4-methylpiperazin-1-yl)sulfonyl)-4-phenyl-4,5-dihydro-1H-pyrazole-1-carboximidothioic acid methyl ester (4.24 gram, 76% yield) as an amorphous solid. ($R_f$~0.1, EtOAc/methanol=95/5 (v/v)).

In an analogous manner the compounds having formula (Ib) listed below have been prepared:

95. 3-(4-Chlorophenyl)-N-(((2-(dimethylamino)ethyl)ethylamino)sulfonyl)-4-phenyl-4,5-dihydro-1H-pyrazole-1-carboximidothioic acid methykl ester. MP: 158° C.

96. N-((Diethylamino)sulfonyl)-3-(4-fluorophenyl)-4-phenyl-4,5-dihydro-1H-pyrazole-1-carboximidothioic acid methyl ester. Amorphous. $R_f$~0.4 (MTBE).

EXAMPLE 100

(−)-(4S)-3-(4-Chlorophenyl)-N-methyl-4-phenyl-N'-((piperidin-1-yl)sulfonyl)-4,5-dihydro-1H-pyrazole-1-carboxamidine (−)-(4S)-3-(4-Chlorophenyl)-N-methyl-4-phenyl-N'-((piperidin-1-yl)sulfonyl)-4,5-dihydro-1H-pyrazole-1-carboxamidine (3.8 gram, 8.3 mol)) ($[α^{25}_D]$=−139°, c=0.006, MeOH) was obtained as an amorphous solid via chiral chromatographic separation of racemic 3-(4-chlorophenyl)-N-methyl-4-phenyl-N'-((piperidin-1-yl)sulfonyl)-4,5-dihydro-1H-pyrazole-1-carboxamidine (7.87 gram, 17.1 mmol) using a chiral stationary phase Chiralpak AD. The mobile phase consisted of methanol/diethylamine=999/1 (v/v).

In an analogous manner the optically pure compounds listed below have been prepared from the corresponding racemates:

101. (−)-(4S)-3-(4-Chlorophenyl)-N'-((diethylamino)sulfonyl)-N-methyl-4-phenyl-4,5-dihydro-1H-pyrazole-1-carboxamidine (Chiral stationary phase: Chiralcel OD). Mobile phase consisted of hexane/2-propanol=80/20 (v/v). ($[α^{25}_D]$=−147°, c=0.01, MeOH). Amorphous.

102. (−)-(4S)-3-(4-Chlorophenyl)-N'-((dimethylamino)sulfonyl)-N-methyl-4-phenyl-4,5-dihydro-1H-pyrazole-1-carboxamidine (Chiral stationary phase: Chiralpak AD). The mobile phase consisted of methanol/diethylamine=999/1 (v/v). ($[α^{25}_D]$=−171°, c=0.005, MeOH). Amorphous.

103. (−)-(4S)-3-(4-Chlorophenyl)-N-methyl-N′-((morpholin-4-yl)sulfonyl)-4-phenyl-4,5-dihydro-1H-pyrazole-1-carboxamidine ([$\alpha^{25}_D$]=−144°, c=0.01, MeOH). (Chiral stationary phase: Chiralpak AD). The mobile phase consisted of ethanol. Amorphous.

What is claimed is:

1. A compound of the formula (Ia) or (Ib)

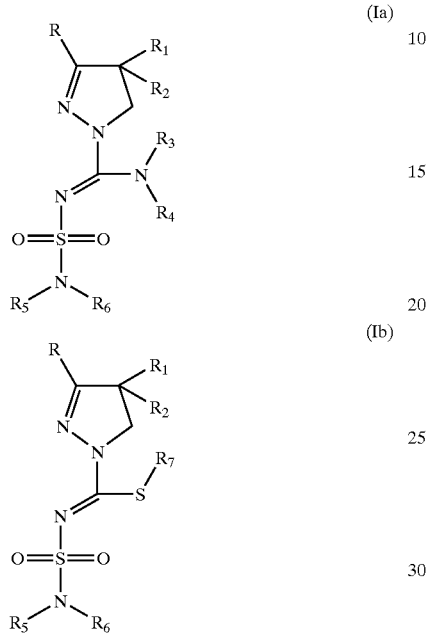

wherein

R and $R_1$ independently represent a phenyl, thienyl or pyridyl group, which groups may be substituted with 1, 2 or 3 substituents Y, which are the same or different, and are chosen from $C_{1-3}$-alkyl and alkoxy, hydroxy, halogen, trifluoromethyl, trifluoromethylthio, trifluoromethoxy, nitro, amino, mono- and dialkyl ($C_{1-2}$)-amino, mono- and dialkyl ($C_{1-2}$)-amido, ($C_{1-3}$)-alkyl sulfonyl, dimethylsulfamido, $C_{1-3}$-alkoxycarbonyl, carboxyl, trifluoromethylsulfonyl, cyano, carbamoyl, sulfamoyl and acetyl, or one or both of R and $R_1$ independently represents naphthyl, $R_2$ represents hydrogen, hydroxy, $C_{1-3}$-alkoxy, acetyloxy or propionyloxy, $R_3$ represents a hydrogen atom or a branched or unbranched $C_{1-8}$ alkyl group or a $C_{3-7}$ cycloalkyl group which alkyl group and cycloalkyl group may be substituted with a hydroxy radical, $R_4$ represents a hydrogen atom or a branched or unbranched $C_{1-8}$ alkyl, $C_{3-8}$ cycloalkyl, $C_{2-10}$ heteroalkyl, $C_{3-8}$ nonaromatic heterocycloalkyl or $C_{4-10}$ nonaromatic heterocycloalkyl-alkyl moiety, which moieties may contain one or more heteroatoms chosen from O, N, and S, which moieties may be substituted with a keto, trifluoromethyl, $C_{1-3}$ alkyl, hydroxy, amino, monoalkylamino, or dialkylamino radical or a fluoro atom, or $R_4$ represents an amino, hydroxy, phenoxy or benzyloxy group, or $R_4$ represents a branched or unbranched $C_{1-8}$ alkoxy, $C_{3-8}$ alkenyl, $C_{5-8}$ cycloalkenyl or $C_{6-9}$ cycloalkenylalkyl group, which groups may contain a sulphur, nitrogen or oxygen atom, a keto radical or a —$SO_2$— radical, which $C_{1-8}$ alkoxy, $C_{3-8}$ alkenyl, $C_{5-8}$ cycloalkenyl and $C_{6-9}$ cycloalkenylalkyl groups may be substituted with a hydroxy, a trifluoromethyl, an amino, a monoalkylamino, a dialkylamino radical or a fluoro atom, or $R_4$ represents a phenyl, benzyl, pyridyl, thienyl, pyridylmethyl or phenethyl group wherein the aromatic rings thereof may be substituted with 1, 2 or 3 of the substituents Y, wherein Y has the meaning as indicated above, or $R_4$ represents a group $NR_8R_9$ with the proviso that $R_3$ represents a hydrogen atom or a methyl group and wherein $R_8$ and $R_9$ are the same or different and represent $C_{1-4}$ alkyl or $C_{2-4}$ trifluoroalkyl or $R_8$ and $R_9$—together with the nitrogen atom to which they are bonded—form a saturated or un-saturated heterocyclic moiety having 4 to 8 ring atoms which heterocyclic moiety may contain an oxygen or sulphur atom or a keto group or —$SO_2$— group or an additional nitrogen atom, which heterocyclic moiety may be substituted with a $C_{1-4}$ alkyl group or $R_3$ and $R_4$—together with the nitrogen atom to which they are bonded—form a saturated or unsaturated, monocyclic or bicyclic heterocyclic moiety having 4 to 10 ring atoms, which heterocyclic moiety may contain one or more species chosen from O, N, S, keto radicals and —$SO_2$— radicals, which heterocyclic moiety may be substituted with a $C_{1-4}$ alkyl, hydroxyalkyl, phenyl, thienyl, pyridyl, amino, monoalkylaminoalkyl, dialkylaminoalkyl, monoalkylamino, dialkylamino, aminoalkyl, azetidinyl, pyrrolidinyl, piperidinyl or hexahydro-1H-azepinyl radical, $R_5$ and $R_6$ independently of each other represent a hydrogen atom or a branched or unbranched $C_{1-8}$ alkyl or alkenyl group, which groups may contain one or more species chosen from O, N, S, keto radicals and —$SO_2$— radicals, and which groups may be substituted with a hydroxy or amino group, or $R_5$ and $R_6$ independently of each other represent a $C_{3-8}$ cycloalkyl group or $C_{3-8}$ cycloalkenyl group, which groups may contain one or more species chosen from O, N, S, and —$SO_2$— radicals and which groups may be substituted with a hydroxy, alkyl ($C_{1-3}$), $SO_2$, keto, amino, monoalkylamino ($C_{1-3}$) or dialkylamino ($C_{1-3}$) radical, or $R_5$ represents a naphthyl group or a phenyl group, which phenyl group may be substituted with 1, 2 or 3 substituents Y, wherein Y has the meaning as described hereinabove, with the proviso that $R_6$ represents a hydrogen atom, or $R_5$ represents a branched or unbranched alkyl group ($C_{1-5}$) which alkyl group may contain one or more species chosen from O, N, S, and —$SO_2$— radicals, and which alkyl group may be substituted with a hydroxy, keto or amino radical, or $R_5$ and $R_6$, together with the nitrogen atom to which they are bonded, form a monocyclic, bicyclic or tricyclic alkyl or alkenyl group which may contain one or more species chosen from O, N, S, keto radicals and —$SO_2$— radicals, and which monocyclic, bicyclic or tricyclic alkyl or alkenyl group may be substituted with a hydroxy, alkyl ($C_{1-3}$), $SO_2$, keto, amino, monoalkylamino ($C_{1-3}$), dialkylamino ($C_{1-3}$), pyrrolidinyl or piperidinyl radical, which monocyclic, bicyclic or tricyclic alkyl or alkenyl group may contain an annelated phenyl group, which annelated phenyl group may be substituted with 1 or 2 substituents Y, wherein Y has the meaning as described herein above, $R_7$ represents a branched or unbranched $C_{1-3}$ alkyl group, or a tautomer, stereoisomer, prodrug, or salt thereof.

2. A pharmaceutical composition comprising an effective amount of at least one compound as claimed in claim 1 as an active component, and at least one auxiliary substance, liquid carrier material, or solid carrier material, or a mixture of two or more of the foregoing.

3. A process for preparing the pharmaceutical composition as claimed in claim 2, comprising mixing the at least one compound with the at least one auxiliary substance, liquid carrier material, or solid carrier material, or a mixture of two or more of the foregoing, to yield a form suitable for administration.

4. A process for the preparation of a compound having formula (Ib) as claimed in claim 1, wherein R, $R_1$, $R_2$, $R_5$, $R_6$, and $R_7$ have the meanings given in claim 1, the process comprising:

1) reacting a compound having formula (III)

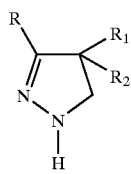
(III)

with a compound having formula (IV)

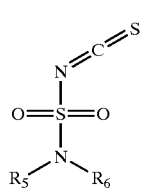
(IV)

to yield a compound of the formula (V)

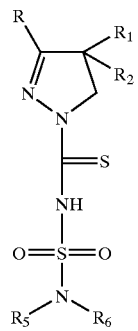
(V)

which is reacted with a compound of the formula $R_7$—X, in which X is a leaving group, or 2) reacting a compound having formula (III) with a compound having formula (IX)

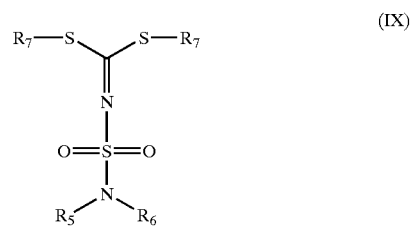
(IX)

to yield the compound of formula (Ib).

5. A process for the preparation of a compound having formula (Ia) as claimed in claim 1, wherein R, $R_1$, $R_2$, $R_3$, $R_4$, $R_5$, and $R_6$ have the meanings given in claim 1, the process comprising:

1) reacting a compound having formula (Ib) as set forth in claim 1, with an amine of the formula $HNR_3R_4$, or 2) reacting a compound having formula (V)

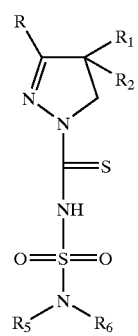
(V)

with an amine of the formula $HNR_3R_4$ in the presence of a mercury (II) salt, or 3) reacting a compound having formula (III)

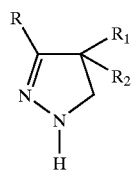
(III)

with a compound of the formula (VI)

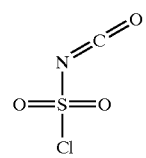
(VI)

followed by treating with an amine of the formula $HNR_5R_6$, to yield a compound of the formula (VII)

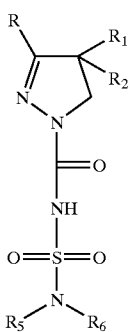

(VII)

which is reacted with a halogenating agent to yield a compound of the formula (VIII)

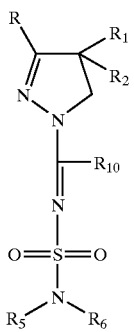

(VIII)

wherein $R_{10}$ represents a halogen atom,
which is reacted with an amine of the formula $HNR_3R_4$, to yield the compound of formula (Ia).

6. A compound of the formula (V)

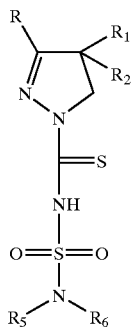

(V)

wherein
R and $R_1$ independently represent a phenyl, thienyl or pyridyl group, which groups may be substituted with 1, 2 or 3 substituents Y,
which are the same or different, and are chosen from $C_{1-3}$-alkyl and alkoxy, hydroxy, halogen, trifluoromethyl, trifluoromethylthio, trifluoromethoxy, nitro, amino, mono- and dialkyl $(C_{1-2})$-amino, mono- and dialkyl $(C_{1-2})$-amido, $(C_{1-3})$-alkyl sulfonyl, dimethylsulfamido, $C_{1-3}$-alkoxycarbonyl, carboxyl, trifluoromethylsulfonyl, cyano, carbamoyl, sulfamoyl and acetyl,
or one or both of R and $R_1$ independently represents naphthyl, $R_2$ represents hydrogen, hydroxy, $C_{1-3}$-alkoxy, acetyloxy or propionyloxy, $R_5$ and $R_6$ independently of each other represent a hydrogen atom or a branched or unbranched $C_{1-8}$ alkyl or alkenyl group, which groups may contain one or more species chosen from O, N, S, keto radicals and —$SO_2$— radicals, and which groups may be substituted with a hydroxy or amino group, or $R_5$ and $R_6$ independently of each other represent a $C_{3-8}$ cycloalkyl group or $C_{3-8}$ cycloalkenyl group, which groups may contain one or more species chosen from O, N, S, and —$SO_2$— radicals and which groups may be substituted with a hydroxy, alkyl $(C_{1-3})$, $SO_2$, keto, amino, monoalkylamino $(C_{1-3})$ or dialkylamino $(C_{1-3})$ radical, or $R_5$ represents a naphthyl group or a phenyl group, which phenyl group may be substituted with 1, 2 or 3 substituents Y, wherein Y has the meaning as described hereinabove, with the proviso that $R_6$ represents a hydrogen atom, or $R_5$ represents a branched or unbranched alkyl group $(C_{1-5})$ which alkyl group may contain one or more species chosen from O, N, S, and —$SO_2$— radicals, and which alkyl group may be substituted with a hydroxy, keto or amino radical, or $R_5$ and $R_6$, together with the nitrogen atom to which they are bonded, form a monocyclic, bicyclic or tricyclic alkyl or alkenyl group which may contain one or more species chosen from O, N, S, keto radicals and —$SO_2$— radicals, and which monocyclic, bicyclic or tricyclic alkyl or alkenyl group may be substituted with a hydroxy, alkyl $(C_{1-3})$, $SO_2$, keto, amino, monoalkylamino $(C_{1-3})$, dialkylamino $(C_{1-3})$, pyrrolidinyl or piperidinyl radical, which monocyclic, bicyclic or tricyclic alkyl or alkenyl group may contain an annelated phenyl group, which annelated phenyl group may be substituted with 1 or 2 substituents Y, wherein Y has the meaning as described herein above, or a tautomer, stereoisomer, or salt thereof.

7. A compound of the formula (VII)

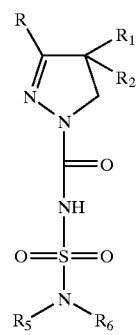

(VII)

wherein
R and $R_1$ independently represent a phenyl, thienyl or pyridyl group, which groups may be substituted with 1, 2 or 3 substituents Y,
which are the same or different, and are chosen from $C_{1-3}$-alkyl and alkoxy, hydroxy, halogen, trifluoromethyl, trifluoromethylthio, trifluoromethoxy, nitro, amino, mono- and dialkyl $(C_{1-2})$-amino, mono- and dialkyl $(C_{1-2})$-amido, $(C_{1-3})$-alkyl sulfonyl, dimethylsulfamido, $C_{1-3}$-alkoxycarbonyl, carboxyl, trifluoromethylsulfonyl, cyano, carbamoyl, sulfamoyl and acetyl, or one or both of R and $R_1$ independently represents naphthyl, $R_2$ represents hydrogen, hydroxy, $C_{1-3}$-alkoxy, acetyloxy or propionyloxy, $R_5$ and $R_6$ independently of each other represent a hydrogen atom or a branched or unbranched $C_{1-8}$ alkyl or alkenyl group, which groups may contain one or more species chosen from O, N, S, keto radicals and —$SO_2$— radicals, and which groups may be substituted with a hydroxy or amino group, or $R_5$ and $R_6$ independently of each other represent a $C_{3-8}$ cycloalkyl group or $C_{3-8}$ cycloalkenyl group, which groups may contain one or more species chosen from O, N, S, and —$SO_2$— radicals and which groups may be substituted with a hydroxy, alkyl ($C_{1-3}$), $SO_2$, keto, amino, monoalkylamino ($C_{1-3}$) or dialkylamino ($C_{1-3}$) radical, or $R_5$ represents a naphthyl group or a phenyl group, which phenyl group may be substituted with 1, 2 or 3 substituents Y, wherein Y has the meaning as described hereinabove, with the proviso that $R_6$ represents a hydrogen atom, or $R_5$ represents a branched or unbranched alkyl group ($C_{1-5}$) which alkyl group may contain one or more species chosen from O, N, S, and —$SO_2$— radicals, and which alkyl group may be substituted with a hydroxy, keto or amino radical, or $R_5$ and $R_6$, together with the nitrogen atom to which they are bonded, form a monocyclic, bicyclic or tricyclic alkyl or alkenyl group which may contain one or more species chosen from O, N, S, keto radicals and —$SO_2$— radicals, and which monocyclic, bicyclic or tricyclic alkyl or alkenyl group may be substituted with a hydroxy, alkyl ($C_{1-3}$), $SO_2$, keto, amino, monoalkylamino ($C_{1-3}$), dialkylamino ($C_{1-3}$), pyrrolidinyl or piperidinyl radical, which monocyclic, bicyclic or tricyclic alkyl or alkenyl group may contain an annelated phenyl group, which annelated phenyl group may be substituted with 1 or 2 substituents Y, wherein Y has the meaning as described herein above, or a tautomer, stereoisomer, or salt thereof.

8. A compound of the formula (VIII)

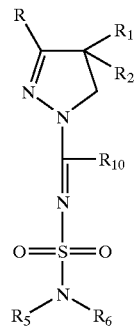

(VIII)

wherein

R and $R_1$ independently represent a phenyl, thienyl or pyridyl group, which groups may be substituted with 1, 2 or 3 substituents Y, which are the same or different, and are chosen from $C_{1-3}$-alkyl and alkoxy, hydroxy, halogen, trifluoromethyl, trifluoromethylthio, trifluoromethoxy, nitro, amino, mono- and dialkyl ($C_{1-2}$)-amino, mono- and dialkyl ($C_{1-2}$)-amido, ($C_{1-3}$)-alkyl sulfonyl, dimethylsulfamido, $C_{1-3}$-alkoxycarbonyl, carboxyl, trifluoromethylsulfonyl, cyano, carbamoyl, sulfamoyl and acetyl, or one or both of R and $R_1$ independently represents naphthyl, $R_2$ represents hydrogen, hydroxy, $C_{1-3}$-alkoxy, acetyloxy or propionyloxy, $R_5$ and $R_6$ independently of each other represent a hydrogen atom or a branched or unbranched $C_{1-8}$ alkyl or alkenyl group, which groups may contain one or more species chosen from O, N, S, keto radicals and —$SO_2$— radicals, and which groups may be substituted with a hydroxy or amino group, or $R_5$ and $R_6$ independently of each other represent a $C_{3-8}$ cycloalkyl group or $C_{3-8}$ cycloalkenyl group, which groups may contain one or more species chosen from O, N, S, and —$SO_2$— radicals and which groups may be substituted with a hydroxy, alkyl ($C_{1-3}$), $SO_2$, keto, amino, monoalkylamino ($C_{1-3}$) or dialkylamino ($C_{1-3}$) radical, or $R_5$ represents a naphthyl group or a phenyl group, which phenyl group may be substituted with 1, 2 or 3 substituents Y, wherein Y has the meaning as described hereinabove, with the proviso that $R_6$ represents a hydrogen atom, or $R_5$ represents a branched or unbranched alkyl group ($C_{1-5}$) which alkyl group may contain one or more species chosen from O, N, S, and —$SO_2$— radicals, and which alkyl group may be substituted with a hydroxy, keto or amino radical, or $R_5$ and $R_6$, together with the nitrogen atom to which they are bonded, form a monocyclic, bicyclic or tricyclic alkyl or alkenyl group which may contain one or more species chosen from O, N, S, keto radicals and —$SO_2$— radicals, and which monocyclic, bicyclic or tricyclic alkyl or alkenyl group may be substituted with a hydroxy, alkyl ($C_{1-3}$), $SO_2$, keto, amino, monoalkylamino ($C_{1-3}$), dialkylamino ($C_{1-3}$), pyrrolidinyl or piperidinyl radical, which monocyclic, bicyclic or tricyclic alkyl or alkenyl group may contain an annelated phenyl group, which annelated phenyl group may be substituted with 1 or 2 substituents Y, wherein Y has the meaning as described herein above, and wherein $R_{10}$ represents a halogen atom, or a tautomer, stereoisomer, or salt thereof.

9. A method of treating at least one disorder involving cannabinoid neurotransmission in a patient in need of such treating, comprising administering to the patient at least one compound as claimed in claim 1 in an amount effective for treating the patients, wherein the at least one disorder is chosen from anxiety, depression, obesity, asthma, and appetite disorders.

* * * * *